United States Patent
Kopes (10) Patent No.: US 9,795,502 B1
(45) Date of Patent: Oct. 24, 2017

(54) CONTROLLABLE HEATED MASK

(71) Applicant: Tiberiu Kopes, Zug (CH)

(72) Inventor: Tiberiu Kopes, Zug (CH)

( * ) Notice: Subject to any disclaimer, the term of this patent is extended or adjusted under 35 U.S.C. 154(b) by 0 days.

(21) Appl. No.: 15/406,721

(22) Filed: Jan. 15, 2017

Related U.S. Application Data (63) Continuation of application No. 15/260,142, filed on Sep. 8, 2016.

(51) Int. Cl.
*A61F 7/00* (2006.01)

(52) U.S. Cl.
CPC ...... *A61F 7/007* (2013.01); *A61F 2007/0003* (2013.01); *A61F 2007/0006* (2013.01); *A61F 2007/0007* (2013.01); *A61F 2007/0077* (2013.01); *A61F 2007/0086* (2013.01); *A61F 2007/0096* (2013.01)

(58) Field of Classification Search
CPC combination set(s) only.
See application file for complete search history.

(56) References Cited

U.S. PATENT DOCUMENTS

| | | | | |
|---|---|---|---|---|
| 2,038,275 A | * | 4/1936 | Fogg | H05B 3/342 165/46 |
| 2,635,175 A | * | 4/1953 | Hodge | A61F 7/007 219/528 |
| 4,021,640 A | * | 5/1977 | Gross | A41D 19/01535 2/159 |
| 4,702,235 A | * | 10/1987 | Hong | A61F 5/028 128/DIG. 20 |
| 7,707,655 B2 | | 5/2010 | Braunecker | |
| 2002/0153367 A1 | * | 10/2002 | Haas, Jr. | A41D 13/0051 219/543 |
| 2011/0208279 A1 | | 8/2011 | Sanker | |
| 2012/0222192 A1 | * | 9/2012 | Carey | A61F 7/02 2/171.2 |
| 2013/0007945 A1 | | 1/2013 | Krondahl | |
| 2013/0281893 A1 | | 10/2013 | Yang | |
| 2015/0012073 A1 | * | 1/2015 | Devine | A61F 7/007 607/109 |

(Continued)

FOREIGN PATENT DOCUMENTS

WO WO 2014/134369 * 9/2014

*Primary Examiner* — Joseph Stoklosa
*Assistant Examiner* — Adam Avigan
(74) *Attorney, Agent, or Firm* — Continuum Law; Robert P. Cogan (57) ABSTRACT

A heated mask comprises a user-operated control providing a number of different parameters including temperature and duration of heat application. At least one area contains a heater element. The heated mask covers an upper portion of a face and has areas positioned to be in registration with sinuses of a user. The heating element in one form comprises a serpentine conductor having a path through each area and having a preselected resistance in each area. In another form, a plurality of separate electrodes are provided, each in one selected area. Each electrode section is separately controlled to provide a preselected level of heat. It has been found that selected temperatures for a heater provide relief for sinus congestion, and that particular combinations of relative setting of a plurality of electrodes are associated with enhanced therapeutic results.

8 Claims, 9 Drawing Sheets

(56) References Cited

U.S. PATENT DOCUMENTS

2016/0015559 A1\* 1/2016 Whitsett ................ A61F 7/007
                                                      607/108
2016/0051402 A1  2/2016 Laghi
2016/0100977 A1  4/2016 Lee \* cited by examiner

_CONTROLLABLE HEATED MASK_

CROSS-REFERENCE TO RELATED APPLICATIONS

This application is a continuation application of U.S. patent application Ser. No. 15/260,142 filed on Sep. 8, 2016 "CONTROLLABLE HEATED MASK" which is incorporated herein by reference in its entirety.

FIELD

The present subject matter relates generally to thermal application to a particular body area and more specifically to a face heated mask for application of heat to sinus cavities of a user.

BACKGROUND

Heated masks are used in a wide variety of applications. Heat may be applied to relax a user. Aroma therapy could be provided. However, heated masks do not generally provide for specific forms of sinus therapy. Prior heated masks have functional limitations in modes of applying heat or in modes of use.

For example, U.S. Pat. No. 7,707,655 discloses a self-warming heated mask. The self-warming heated mask includes a facing layer configured to cover at least a portion of a person's face. Attached to the facing layer is at least one thermal delivery pad containing an exothermic composition. Upon removal from a package, air activates the thermal delivery pad and elevates temperature of the heated mask. The heated mask may be used in conjunction with a fragrance or vapor delivery device. Temperature excursions and amount of heat are determined by the formulation and amount of the exothermic composition. The temperature variation cannot be controlled.

United States Published Patent Application No. 20160051402 discloses a post-surgical treatment heated mask comprising a thermoform able resin arranged on a knitted fabric layer which can be shaped to conform to contours of a user's face. The heated mask must be heated or cooled in an external heat exchange environment prior to placing the heated mask on the user to change the temperature of the user's face. Duration of temperature application cannot be controlled.

United States Published Patent Application No. 20160100977 discloses heating devices for medical treatment which include a polymer matrix comprising a polymer and a plurality of electrically conductive particles distributed within the polymer. The matrix is connected between two electrodes. While heating may be controlled, special materials must be used for construction and special containers must be used for the electrically conductive particles. Consequently, expense in manufacturing is increased.

United States Published Patent Application No. 20130281893 discloses an eye heated mask for applying heat to a user. However, this apparatus uses circulating water and a heat exchanger. This device is complex in construction and presents a time lag between selecting a temperature and changing temperature of the water.

United States Published Patent Application No. 20110208279 discloses a mucociliary clearance apparatus which delivers heat into the lungs main bronchi down to the final branchings of the respiratory tree which include cilia. A heating element is affixed to the head and is maintained only at a temperature slightly above normal body temperature. Heat is applied to the lungs and not to the sinuses.

United States Published Patent Application No. 20130007945 discloses a faceheated mask covering an entire face which ties around the head. Heat is provided by an electrical heater settable at a low, medium, or high level. The electrical heater provides one of a plurality of preselected temperatures. No correlation of use of heat to a particular purpose is disclosed.

SUMMARY

Briefly stated, in accordance with the present subject matter, a heated mask. A heated mask is provided comprising a user-operated control for a number of different parameters including temperature and duration of heat application.

The heated mask covers an upper portion of a face and has areas positioned to be in registration with sinuses of a user. At least one area contains a heater element. The heater element in one form comprises a serpentine conductor having a path through each area and having a preselected resistance in each area. In another form, a plurality of separate electrodes are provided, each in one area. Each electrode section is separately controlled to provide a preselected level of heat. It has been found that selected temperatures for a heater provide relief for sinus congestion, and that particular combinations of relative setting of a plurality of electrodes are associated with enhanced therapeutic results.

BRIEF DESCRIPTION OF THE DRAWINGS

The present subject matter may be further understood by reference to the following description taken in connection with the following drawings.

DETAILED DESCRIPTION

A self-heating heated mask according to the present subject matter warms selected areas of a user's face to alleviate symptoms of congestion and sinusitis. The structure provides for comfort, having adjustable straps for helping the heated mask to stay comfortably in place. A bendable nose area provides a snug custom fit so that efficiency of heat transfer from the heated mask to a user's nose is maximized.

Safety features facilitate the user's ability to sleep while wearing the heated mask. A preferred embodiment operates off of a 12-volt power supply. A circuit breaker may be provided to respond to power surges and heated mask temperature exceeding a preselected threshold.

Pulse width modulation may be used to control voltage level applied to heating elements. Control of the voltage level provides accuracy and precision in heated mask temperature in response to temperature selection and minimizes hysteresis.

In one form, the heated mask is powered by line current stepped down to 12 volts. Nominal power is 18 watts. A control module regulates a selectable voltage supplied to a heating element. Each selectable voltage produces a corresponding temperature in the heated mask. In one embodiment, the heating element is divided into sections. Each section is in registration with a selected area or plurality of areas of a user's face. Each area of the face is primarily associated with heating of a corresponding sinus or sinuses. One or more of the heating element sections are selectively energizable. Temperature selection is selectable for each section. Consequently, sinuses to be heated are selectable. In accordance with the present subject matter, it has been found that best results are provided in a heated mask that heats forehead sinuses, nose, and maxillary sinuses. Therapeutic results were also obtained with heat applied only to the nose and maxillary sinuses.

In another form, the heated mask is coupled to USB port of a personal computer for power input. A nominal power level supplied from a USB port of a personal computer is 2.5 watts. In this embodiment, the heated mask is heated to a lower, substantially fixed temperature. The level of heat can be provided without the use of a temperature controller.

Figure 1:
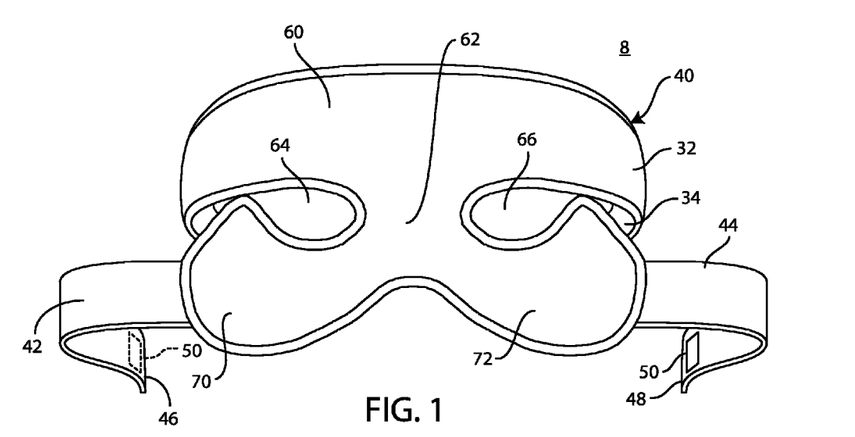
FIG. 1 is an illustration of a heated mask constructed in accordance with the present subject matter.
Figure 2:
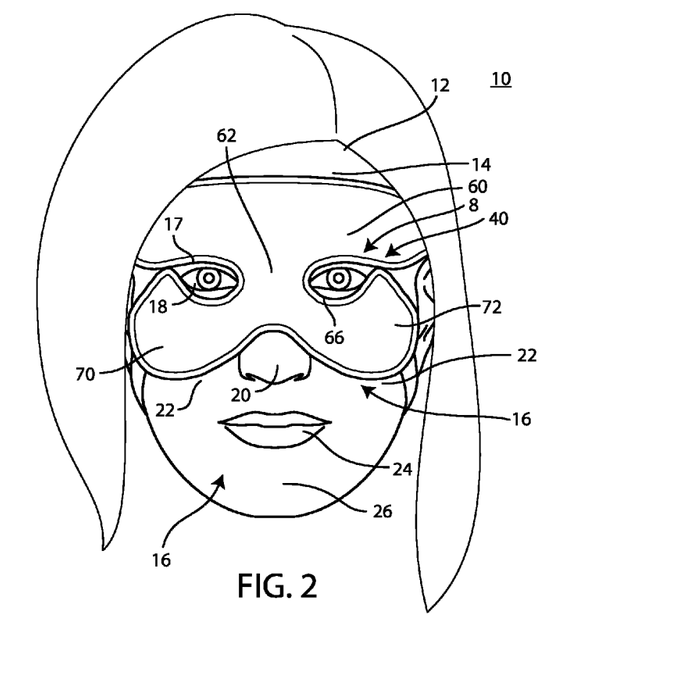
FIG. 2 illustrates a user wearing the heated mask.

FIG. 1 is an illustration of a heated mask 8 constructed in accordance with the present subject matter. FIG. 2 illustrates a user 10 wearing the heated mask 8. FIGS. 1 and 2 are discussed together. The heated mask 8 has a main body 40 covering at least part of a face 16 of the user 10. The face 16 is characterized as comprising separate parts of a user's head 12. The parts correspond to the portions normally associated with each part. In the present description, boundaries between parts are not specifically defined. Specific definition is not required for proper functioning of the present apparatus.

In the present description, the user's face is characterized a comprising a forehead 14, left eyebrow 17, right eyebrow 18, left eye 19, right eye 20, nose 21 and left cheek 22, and right cheek 23. The user 10's mouth 24 and chin 26 will generally be uncovered.

The heated mask comprises a front layer 32 and a back layer 34. The terms front and back are arbitrary. As used in this illustration, the back layer 34 is made for contacting the user 10 and the front layer 32 is an external layer. The heated mask 8 further comprises a first fastening strap 42 and a second fastening strap 44 each having an end fastened to an opposite horizontal end of the main body 40. Terms such as horizontal are used only to define relative locations of components; they are not related to any particular set of orthogonal axes. Ends 46 and 48 of the straps 42 and 44 respectively are provided with fasteners 50 and 52 respectively to maintain the heated mask 8 in engagement with the head 12 of the user 10. The fasteners 50 and 52 in one preferred embodiment comprise a hook and mesh fastener pair generally known under the trademark Velcro®. In one preferred form, the heated mask main body 40 is made of fleece and cotton.

The heated mask 40 may be provided in a variety of sizes. In one preferred embodiment, the heated mask 40 is made in a "one size fits most" configuration. The size is characterized by distance from one pupil of a user 10's eye 18 to the other. In an adult version, the pupillary distance is 70 mm. In a child's version, the pupillary distance is 55 mm.

The main body 40 has areas in registration with selected parts of the user 10's head 12. A forehead area 60 of the main body 40 covers the eyebrows 16 and 17 and a selected extent of the forehead 14. A nasal area 62 covers all or part of the bridge of the nose 20. Eyeholes 64 and 66 may be defined by a perimeter of the heated mask 8. First and second cheek portions 70 and 72 are respectively located under the left eye 19 and the right eye 20.

Figure 3:
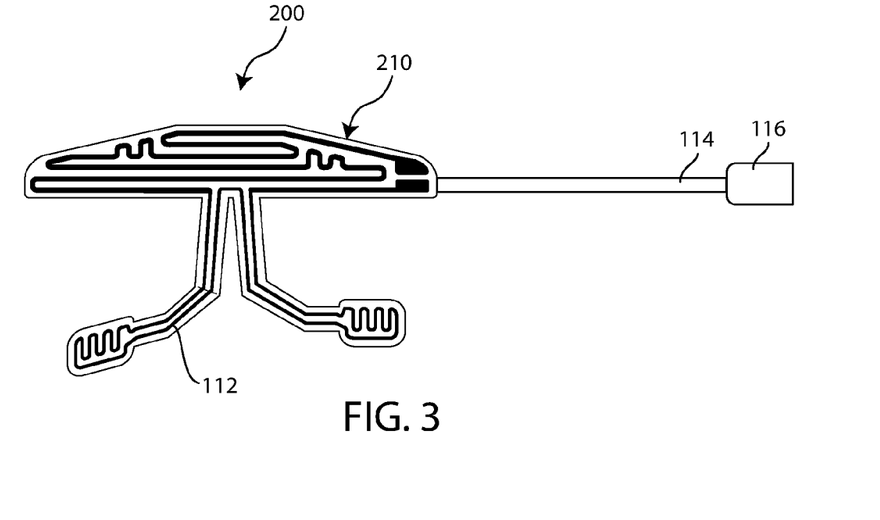
FIG. 3 is an illustration of a heating element and power cable for the heated mask.
Figure 4:
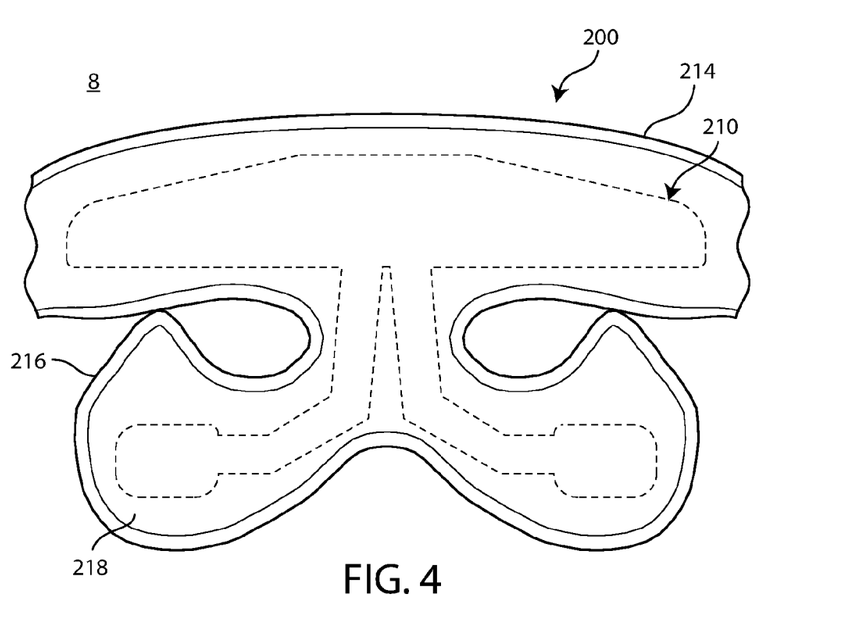
FIG. 4 is a plan view of a heating element for inclusion in the heated mask of FIG. 1 shown within an outline of the heated mask.
Figure 6:
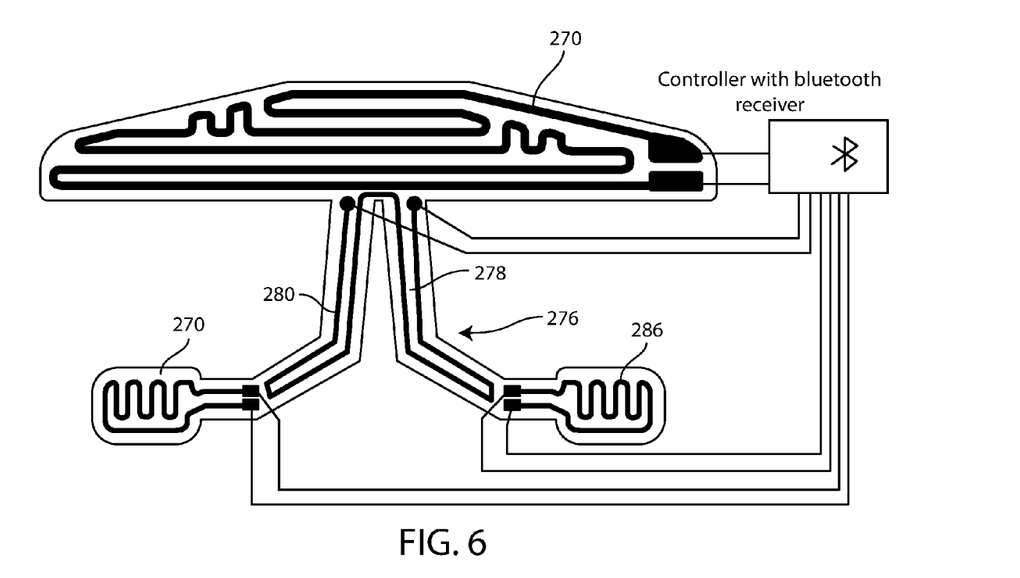
FIG. 6 is a schematic diagram of a second embodiment of the heating element.

FIGS. 3 and 4 are discussed together. FIG. 3 is an illustration of a heating element and power cable for the heated mask. FIG. 4 is a plan view of a heating element for inclusion in the heated mask of FIG. 1 shown within an outline of the heated mask. A heater 100 comprises a substrate 110 and a heating element 112. In FIG. 4, the heater 100 is shown within an outline 114 of the heated mask 8. A perimeter 116 and a stitching line 118 are also illustrated. The main body 40 (FIG. 1) of the heated mask 8 is sewn around the heater 100 along the stitching line 118 (FIG. 6). Clearance is provided between the heater 100 and the stitching line 118. One nominal value for the clearance is 4 mm.

The heating element 112 is mounted to the substrate 110. The heating element 112 may be formed as a circuit trace or may be a discrete component fixed to the substrate 110 by an adhesive. The heating element 112 includes a thermal fuse 124 which will break the circuit in the event of overheating.

The heating element 112 preferably comprises ribbon-like circuit traces. The heating element 112 is a continuous serpentine ribbon starting at a first terminal 140 and ending at a second terminal 144. The terminals 140 and 144 are connected to a socket 146. A power cable 148 is connected to the socket 146. In one preferred form, the socket 146 comprises a USB Micro-B 5 pin jack 148.

Figure 7:
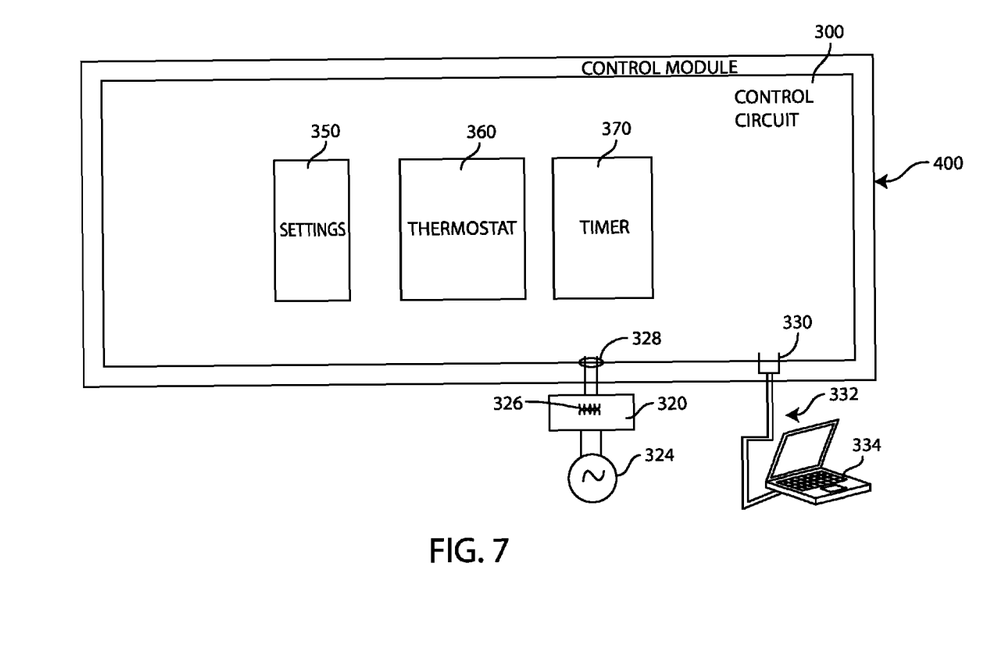
FIG. 7 is a schematic diagram of a system incorporating and controlling the heated mask comprising the first embodiment of the heating element.

The heater 100 comprises a first cheek area 160 and a second cheek area 162. A first nose area 168 and a second nose area 160 are housed within the nose area 62 (FIG. 1). A forehead area 170 is housed within the forehead area 60 of the heated mask 8. In a preferred embodiment heat is uniformly distributed over the heater 100. Operating parameters are selected and controlled from a control module 400 (FIG. 7).

Figure 5:
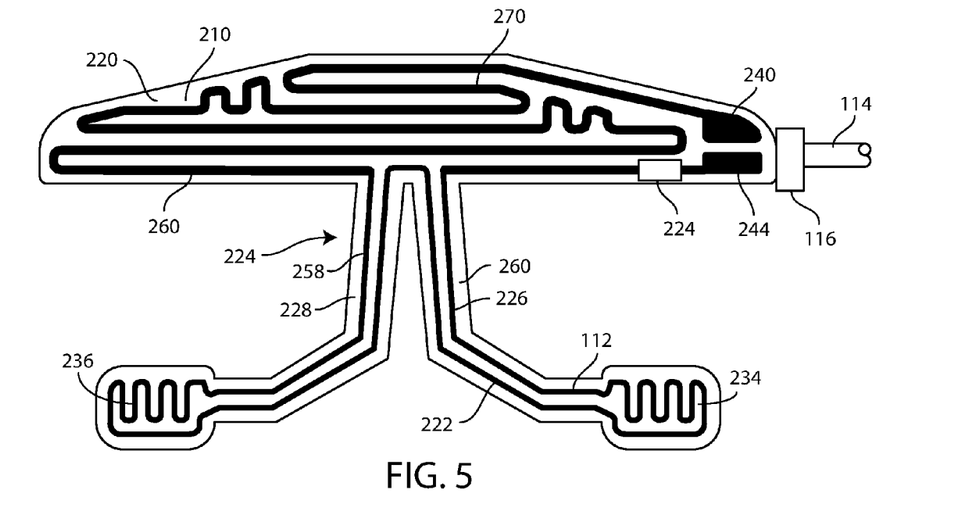
FIG. 5 is a schematic diagram of a first embodiment of the heating element.

FIG. 5 and FIG. 6 are illustrations of a first embodiment and a second embodiment of the heating element 112 respectively. In FIG. 5 and FIG. 6, the same reference numerals are used to denote corresponding elements. The heating element 112 comprises a forehead section 220, a nose section 224 including first and second side sections 226 and 228 for engaging opposite sides of the bridge of the nose 20 (FIG. 1), and first and second cheek sections 234 and 236. The heating element 112 may be divided into more or fewer sections in order to cover one or a plurality of sections of the heated mask as illustrated in FIG. 1. The heating element 112 includes a thermal fuse 124 which will break the circuit in the event of overheating. A temperature sensor 180 provides an input for comparison to a thermostat 360 setpoint (FIG. 7).

In the embodiment of FIG. 5, a forehead section 220, a nose section 224 including first and second side sections 226 and 228, and first and second cheek sections 234 and 236 are formed in a single serpentine electrode 260 is determined by resistance of each section. The relative amount of heat provided by each section is determined by relative resistance. In one preferred form, the serpentine electrode 260 comprises a copper conductor having uniform dimensions. Other conductors such as nickel could be used. The electrode 260 is encased in a polyethylene insulating jacket 264.

Resistance is determined in accordance with the length of conductor in a section. Resistance in each area is determined may be increased by providing a length of conductor provided in addition to the shortest path in each section. Alternatively, resistance may be varied by changing dimensions or composition of sections of the electrode 260.

The electrode 260 comprises first and second ends 270 and 272. Most conveniently, the first and second ends 270 and 272 are located at one horizontal side of the forehead section 220, but could be located elsewhere. The first and second ends 270 and 272 are connected to a connector 282 receive power. The connector 282 is incorporated in circuitry as further described below.

In the embodiment of FIG. 6, the sections of the electrode 260 of FIG. 5 are divided into separate electrodes. A forehead electrode 218 corresponds to the forehead section 220. An electrode 230 corresponds to the nose section 224 including the first and second side sections 226 and 228, and first and second cheek sections 234 and 236. A first cheek electrode 240 is provided corresponding to the first cheek section 234. A second cheek electrode 250 is provided corresponding to the second cheek section 236. Each electrode 218, 230, 240, and 250 includes a terminal pair for connection to the control module 400 (FIG. 7).

Dividing the cheek sections into first and second electrodes is optional. Other divisions of the electrode 260 may be made.

FIG. 7 is a schematic diagram of a control circuit 300 coupled to the heated mask 8. The control module 400 further discussed below with respect to FIG. 10 comprises the control circuit 300. The control circuit 300 controls power to the heating element 112.

The control circuit 300 is selectively connected to a first power source 320 or a second power source 332. The first power source 320 provides a voltage to heat the heating element 112 for provision of selectable heat values. The voltage is at a safe level. A nominal safe voltage level is 12 volts. The power source 320 may conveniently use conventional line voltage from a source 324. Nominally, conventional line voltage is from a 110-volt or 230-volt AC source at 50 Hz or 60 Hz, depending on the user 10's location. The input current to the power source 320 is nominally 1 amp. A step-down transformer 326 converts the input voltage to a safe level voltage of 12-volt DC and providing a 1-amp output. In the present illustration, output voltage from the power source 320 is provided at a receptacle 328. As further described below, in the illustrated embodiment, a power input to the heated mask 40 is 18 watts.

A receptacle 330 comprises a USB plug for connection to the second power source 332, which may comprise a personal computer 334. A nominal power output from a personal computer is 2.5 watts. Use of the second power source 130 provides for a lower temperature range available from the heated mask 8. This low range is selected by connection to the second power source 130 without requiring use of other controls.

Figure 10:
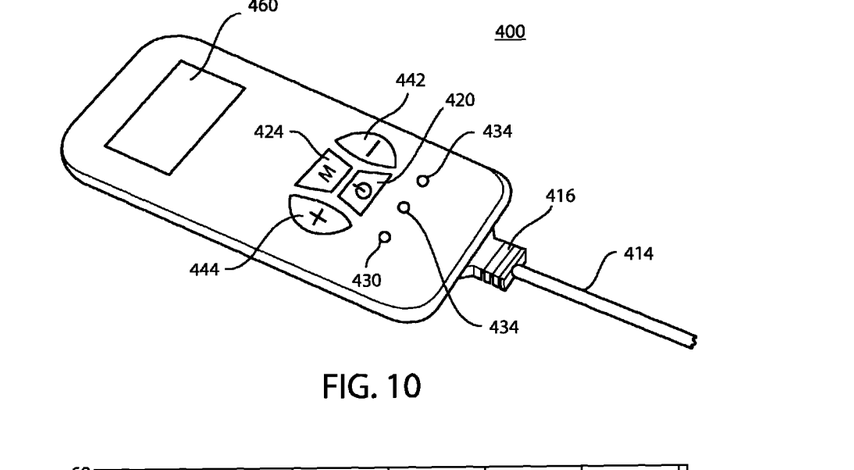
FIG. 10 illustrates a control module.

The control circuit 300 also comprises a setting circuit 350 the operation of which is described with respect to FIG. 10. A thermostat 360 responds to temperature of the heating element 112 and a setting from the setting circuit 350 in order to regulate voltage provided to the heating element 112. A timer 370 responds to settings entered by a user 3 and may also be set to provide an automatic turnoff after a preselected time span. The control circuit 300 preferably comprises a microcircuit chip comprising a processor and storage to perform the above functions. One suitable microcircuit is the Amtel® AVR® ATmega8 by Amtel Corporation, San Jose, Calif.

Figure 8:
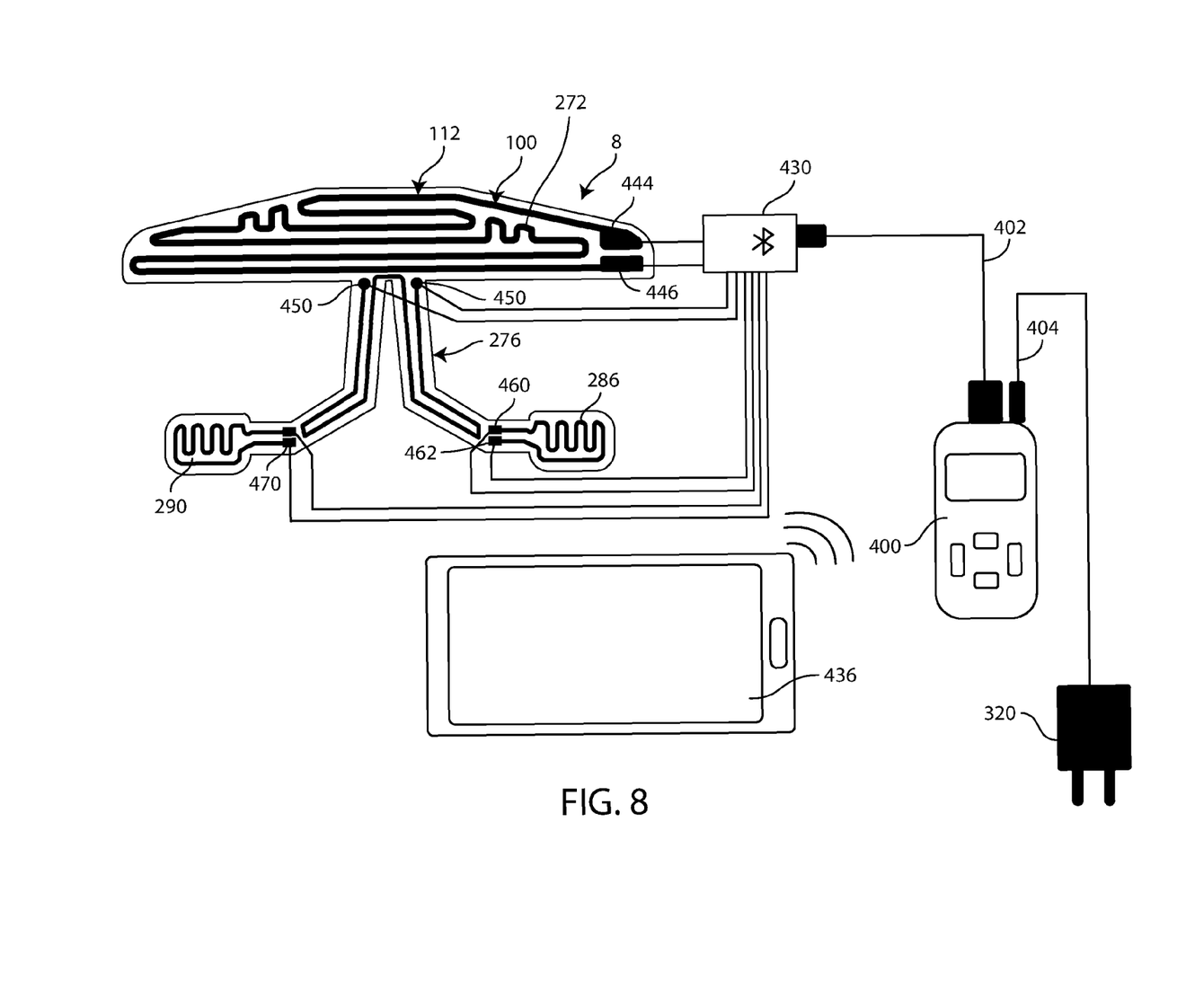
FIG. 8 is a schematic diagram of a system comprising the second embodiment of the heating element powered by a line current source.

FIG. 8 is a schematic diagram of a system comprising the first embodiment of the heating element 112, which is powered by the source 320. The control module 400, discussed further with respect to FIG. 10, receives power from the source 320 and provides an output to control the heater 100 in the mask 8. In the present embodiment, a controller 430 is coupled intermediate the control module 400 and the heater 100. The controller 430 comprises a remote control. The remote control receives input from a remote device 436. The remote control device may conveniently comprise a smart phone or a tablet having an Android or iOs operating system. The remote control device 436 may be programmed with an app duplicating the functions of the control module 400. In this manner, the mask 8 is controlled from a hand-held control module 400 or a remote device 436. The controller 430 is coupled to allow both the control module 400 and the remote device 436 to perform control functions. A preferred form of communication between the remote device 436 and the controller 430 is Bluetooth wireless technology.

Terminals 444 and 446 are provided to connect the forehead electrode 272 to receive power. Terminals 450 and 452 are provided to connect the nose electrode 276 to receive power. Terminals 460 and 462 connect the first cheek electrode 286 to receive power. Terminals 470 and 472 connect the second cheek electrode 290 to receive power. Alternatively, the electrode 260 (FIG. 5) may be resolved into sections corresponding to other face areas.

Often a user may wish to heat only a forehead 14 (FIG. 2). In this case the controller 430 is instructed to close the circuit between terminals 444 and 446. This connection energizes the forehead electrode 272. The connection between each of terminals 450 and 452 to the control circuit 300 is closed in order to energize the nose electrode 276. Similarly, terminals 460 and 462 may be connected to control the first cheek electrode 286. The terminals 470 and 472 are connectable to control the second cheek electrode 290. All or a combination of the electrodes 272, 276, 286, and 290 may be connected to the control circuit 300 at any one time.

Figure 9:
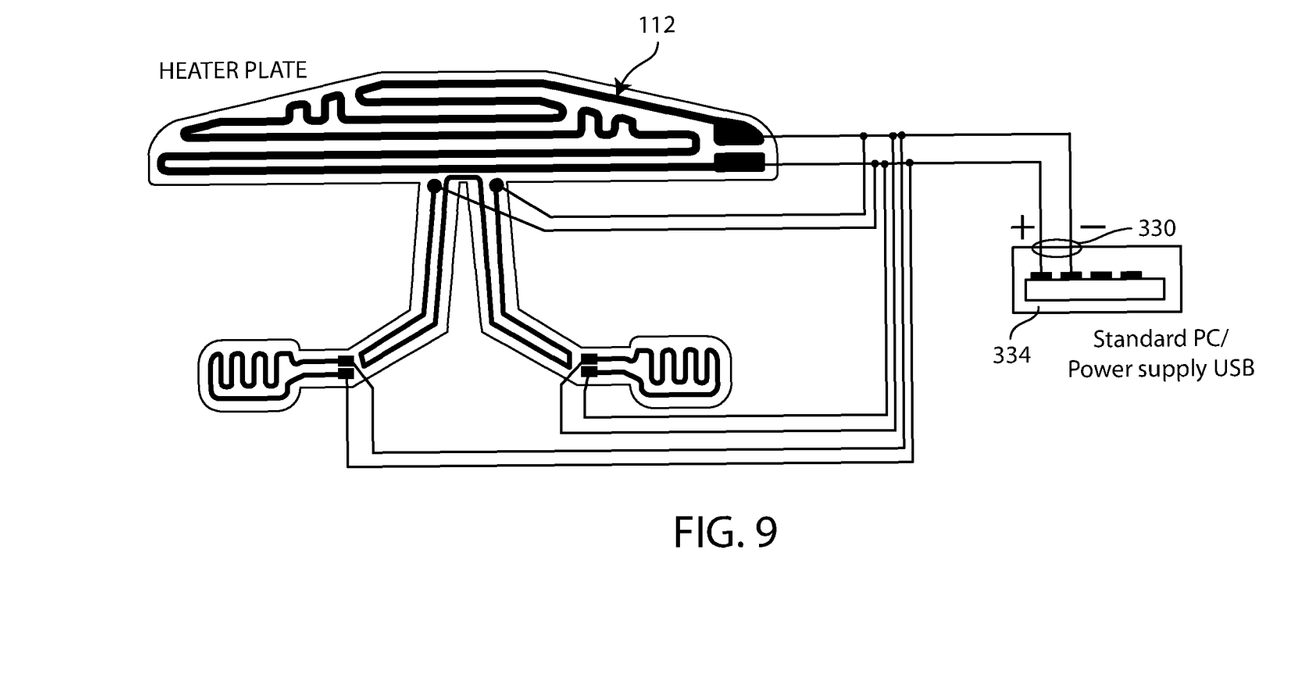
FIG. 9 is a schematic diagram of a system comprising the second embodiment of the heating element powered by a USB output of a personal computer.

FIG. 9 is a schematic diagram of a system comprising the second embodiment of the heating element 112, which is powered by the USB output of the personal computer 334. In this embodiment, the electrodes 272, 276, 286, and 290 are connected in parallel across the receptacle 330. In this manner, the electrodes are all continuously energized. In a different embodiment, these electrodes could be connected in series or in a combination of series and parallel connections.

A nominal power output from a PC USB port is 2.5 watts. The power output provides the capability of heating a face section to a temperature which will generally provide comfort to a user without having to provide the whole temperature range shown in Table I below. The 2.5 watt input in a nominal embodiment could bring the heating element 112 up to a level of 46° C., or 115° F. Since only one level of heat is provided, the level of voltage to the heating element 112 does not have to be selected by the control circuit 300.

FIG. 10 illustrates the control module 400. A power cable 414 is connected for providing input voltage to the control module 400 from a selectable source, such as the sources 320 and 332 in FIG. 7. The power cable 414 is preferably a flat 4-pole or 5-pole cable terminated in a micro USB female plug 416. In one preferred form, the control module 400 comprises an on-off switch 420 and a mode selection button 424. The mode selection button 424 is used to select a current parameter setting mode, such as temperature or time duration of heating. A temperature mode indicator 430, time mode indicator 432, and an on-off indicator 434 are each illuminated when the respective mode is selected. The indicators 430, 432, and 434 preferably comprise light emitting diodes (LEDs). A down adjustment button 442 and an up adjustment button 444 are provided for adjusting a selected level of a current parameter. The control module 400 also comprises a display 460. In an alternative form, parameters represented by the indicators 430, 432, and 434 are instead shown in the display 460. The display 460 may also show the selected temperature and time duration.

The mode selection button 424 may be pressed to enable setting of the time duration for applying heat. In a preferred embodiment, the operating time is settable for between 1 to 12 hours. The user 10 presses the "+" or "−" buttons repeatedly, until the display 460 shows the desired shut off time. At the end of the set time duration, the timer turns the heated mask 8 off so that application of heat is limited in the event that a user 10 falls asleep or forgets to turn off the heating element 112.

After release of all buttons, the controller commands provision of power to the heated mask 8 for the preset time.

A nominal range of temperatures to be provided by the heated mask 8 is 39° C. to 60° C., or 102° F. to 140° F. The range may be achieved by providing a number of steps, the selection of a step determining a selected temperature. In the current illustration, eight steps are provided, as illustrated in Table I. Conversion from Celsius to Fahrenheit is not exact in order to represent each temperature level as an integer. In accordance with the present subject matter, this temperature range has been found to have therapeutic efficacy.

TABLE I

| Step | ° C. | ° F. |
|---|---|---|
| 1 | 39 | 102 |
| 2 | 42 | 108 |
| 3 | 45 | 113 |
| 4 | 48 | 118 |
| 5 | 51 | 124 |
| 6 | 54 | 130 |
| 7 | 57 | 135 |
| 8 | 60 | 140 |

The control circuit 300 may store data such that the display 460 is enabled to display a temperature step in addition to or in the alternative to a temperature reading.

Figure 11:
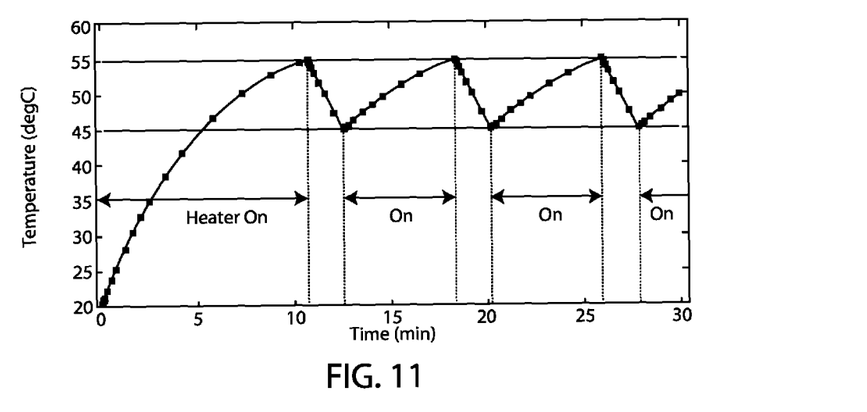
FIG. 11 is a nominal temperature versus time plot for the heated mask.

FIG. 11 is a nominal temperature versus time plot for the heated mask. The abscissa is time in arbitrary units, and the ordinate is temperature in arbitrary units. After starting the heater 200 (FIG. 5), when the heating element 112 is cold, a maximum power level is supplied. The power level is controlled by pulse width modulation. The duty cycle is near 100%, but as the temperature rises the duty cycle begins to decrease. The duty cycle may begin at 100%. Once a working temperature is reached, the duty cycle may go to as low as 2%. At working temperature, only a small fraction of initial power is needed.

Figure 12:
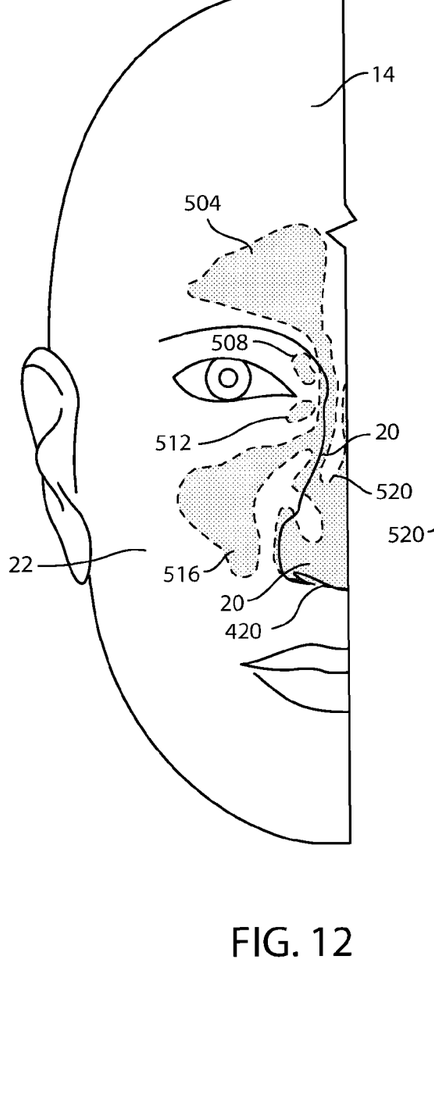
FIG. 12 is an illustration of sinus anatomy showing a healthy sinus condition.
Figure 13:
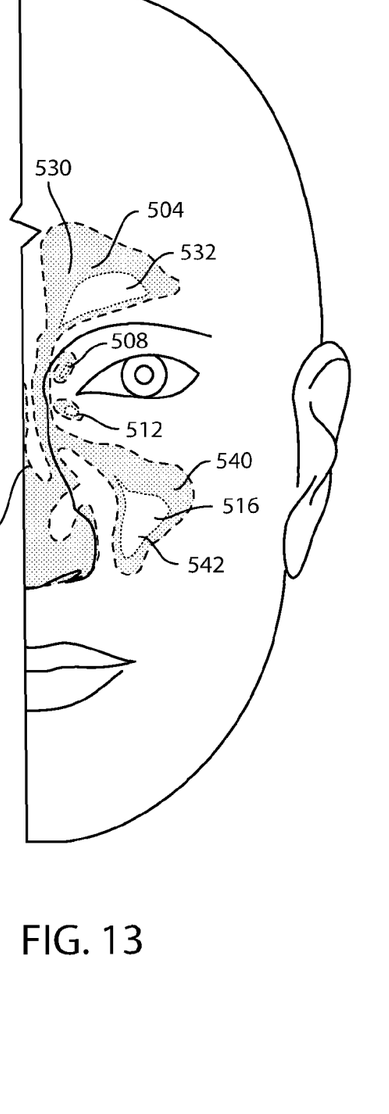
FIG. 13 is an illustration of sinus anatomy manifesting sinusitis.

FIG. 12 is an illustration of sinus anatomy showing a healthy sinus condition, and FIG. 13 is an illustration of sinus anatomy manifesting sinusitis, i.e., nasal inflammation. The same reference numerals are used to denote the healthy sinus and the inflamed sinuses. FIGS. 12 and 13 are taken together. A frontal sinus 504 is at a lower part of the forehead 14. At each side of the nose 20, a sphenoid sinus 508 and an ethmoid sinus 512 are located. A maxillary sinus 516 is located under each cheek 22. The septum 520 is inside the nose 20. In FIG. 12, the sinuses are clear. In FIG. 13, the frontal sinus 504 is illustrated having an inflamed area 530. Excess mucus is at a location 532. Excess mucus and inflammation are also found in the sphenoid sinus 508 and the ethmoid sinus 512. The maxillary sinus 516 is inflamed in an area 540. Excess mucus is in a lower portion of the maxillary sinus 516 at a location 542. The sphenoid sinus 508 and the ethmoid sinus 512 may be referred to collectively as nose sinuses.

Figure 14:
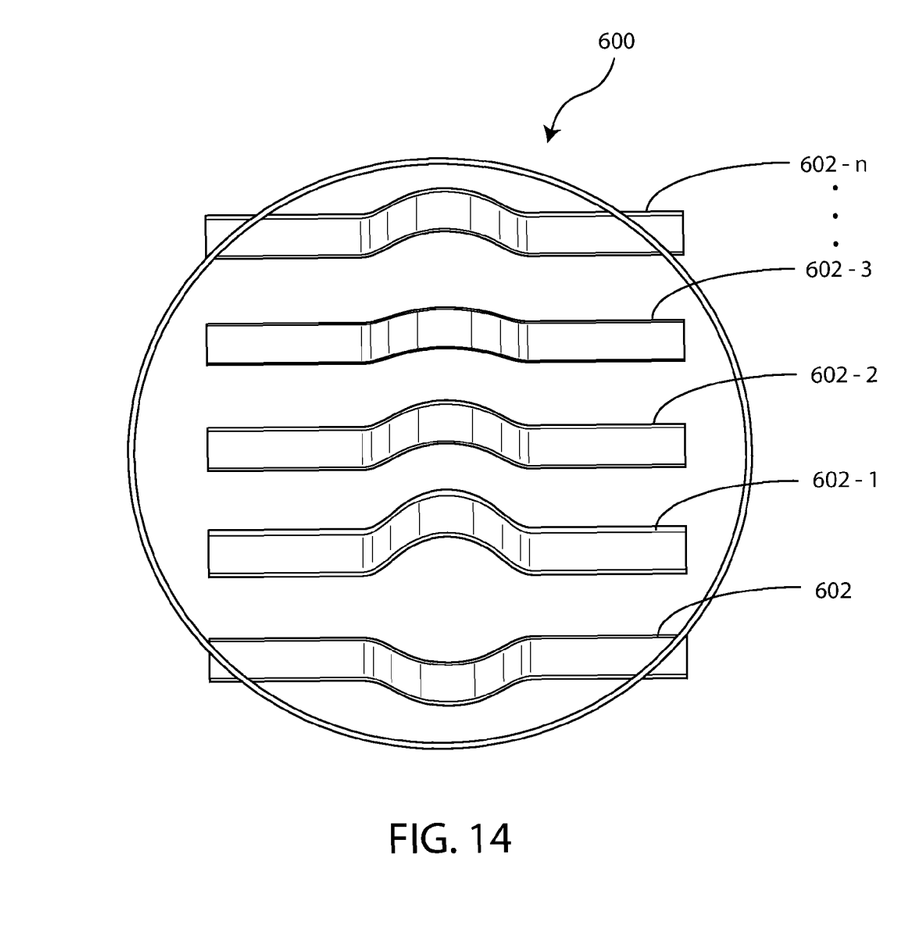
FIG. 14 illustrates components for adjusting fit of the heated mask to the face of a user.

FIG. 14 is a perspective view of a support array 600 used to improve efficiency of heat transfer from the heated mask 8 to the face 16 of a user 10. The support array 600 consists of at least one deformable rib member 602. The deformable rib member 602 is included in nose area 62 (FIG. 1) between the front layer 32 and the back layer 34. Additional rib members 602-1, 602-2, 602-3, and 602-n may be provided where n is an integer. The ribs 602 have a center portion placed over the septum 20 (FIG. 2) and areas extending from the center portion across sides of the nose and the cheeks 22 and 24.

In use, user 10 places the heated mask 8 over the user 10's face and adjusts the straps 42 and 44 (FIG. 1) to a comfortable fit and secures the Velcro fasteners 48 and 50. In order to maximize heat transfer from the heated mask 8 to the user 10, fitting points are provided on either side of the nose area 62 in registration with at least one deformable rib member 602. The rib members 602 are deformed to conform to contours of the user 10's face 16. The deformable rib members 602 will hold the shape of the heated mask 8. The power cable 402 (FIG. 8) is plugged into the control module 400. A power cable 404 has one end plugged into the power source 320 and the other end is plugged into the control module 400.

The present subject matter provides for both comfort levels and therapeutic levels of heat. A low power mode of operation is conveniently provided wherein a user may plug the heated mask into a personal computer. Both manual and remote control may be used.

It is to be understood that although the present invention, has been described with regard to preferred embodiment thereof, various other embodiments and variants may occur to those skilled in the art, which are within the scope and spirit of the invention, and such other embodiments and variants are intended to be covered by the following claims.

The invention claimed is:

1. A controllable heated mask system comprising:
   a mask having a main body shaped for covering at least part of a face of a user, said mask having at least one selected area substantially in registration with at least one sinus;
   said mask comprising a heating element;
   said heating element comprising a first set of conductors;
   a control module storing values of operating parameters and having a control circuit;

a selection circuit to choose a value for at least one of a plurality of operating parameters;

said control module having a first set of terminals and a second set of terminals for selectable connection selectively connecting said first set of conductors to a first power supply or to a second power supply respectively, and providing power to said mask, the control circuit comprising a temperature selection circuit coupled between said first set of terminals and said mask and said control circuit coupling said second set of terminals to said mask to provide a fixed temperature;

a thermostat coupled to the temperature selection circuit, said temperature selection circuit being coupled to provide a setpoint to said thermostat; and a temperature sensor coupled to provide an input to said thermostat indicative of temperature in said mask, wherein said first set of terminals comprises terminals for connection to a first power supply, the first power supply being energized by line voltage, and wherein said second set of terminals comprises a terminal structured for coupling to a USB power port, wherein the heating elements are selected with respect to a power level provided by said first power supply to provide heat at a therapeutic level and to provide heat at a lower level when coupled to the USB power port; and further wherein said control circuit comprises a switch for selectively coupling said second set of terminals to said heating element and bypassing said temperature selection circuit.

2. A controllable heated mask system according to claim 1 wherein said mask is constructed to have areas for heating nose sinuses and maxillary sinuses.

3. A controllable heated mask system according to claim 2 further wherein said mask is constructed to have areas for heating forehead sinuses.

4. A controllable heated mask system according to claim 3 wherein said heating element comprises a nose section including first and second side sections configured to engage opposite sides of a bridge of the nose.

5. A controllable heated mask comprising:
a main body, the mask being shaped for covering at least part of a face of a user, said mask having areas, each area for contacting at least one of a forehead, eyebrows, nose, and cheeks;
a plurality of electrodes, each electrode being retained in one said area and comprising a heating element;
a heating element having a conductor section having a resistance in a preselected ratio to resistance of other conductor sections;
a control module comprising a temperature selection circuit;
said control module having a first set of terminals and a second set of terminals for providing power to said mask and a control circuit for selectively connecting said first set of conductors to a first power supply or to a second power supply respectively;
said temperature selection circuit being coupled between said first set of terminals and said mask and said control circuit coupling said second set of terminals to said mask to provide a fixed temperature;
a thermostat coupled to the temperature selection circuit, said temperature selection circuit being coupled to provide a setpoint to said thermostat;
a temperature sensor coupled to provide an input to said thermostat indicative of temperature in said mask;
wherein said first set of terminals comprises terminals for connection to a first power supply, the first power supply being energized by line current, and wherein said second set of terminals comprises a terminal structured for coupling to a USB power port, wherein the heating elements are selected with respect to a power level provided by said first power supply to provide heat at a therapeutic level and with respect to a power level provided by said second power supply to provide heat at a lower level when coupled to the USB power port; and
wherein said control circuit comprises a switch for selectively coupling said second set of terminals to said heating element and bypassing said temperature selection circuit.

6. A controllable heated mask system according to claim 5 wherein said mask is constructed to have areas for heating nose sinuses and maxillary sinuses.

7. A controllable heated mask system according to claim 6 further wherein said mask is constructed to have areas for heating forehead sinuses.

8. A controllable heated mask system according to claim 7 wherein said heating element comprises a nose section including first and second side sections configured to engage opposite sides of a bridge of the nose.

* * * * *